United States Patent
Zhao et al.

(10) Patent No.: US 11,149,013 B2
(45) Date of Patent: Oct. 19, 2021

(54) CRYSTAL FORM OF URATE TRANSPORTER 1 INHIBITOR AND PREPARATION METHOD AND USE THEREOF

(71) Applicant: Tianjin Institute of Pharmaceutical Research Co., Ltd., Tianjin (CN)

(72) Inventors: Guilong Zhao, Tianjin (CN); Changying Liu, Tianjin (CN); Huihui Chen, Tianjin (CN); Yuquan Li, Tianjin (CN); Haizhi Zhang, Tianjin (CN); Xuyuan Liu, Tianjin (CN); Yuqiang Liu, Tianjin (CN); Yafei Xie, Tianjin (CN); Jingwei Wu, Tianjin (CN); Wei Liu, Tianjin (CN); Weiren Xu, Tianjin (CN); Lida Tang, Tianjin (CN); Meixiang Zou, Tianjin (CN)

(73) Assignee: TIANJIN INSTITUTE OF PHARMACEUTICAL RESEARCH CO., LTD., Tianjin (CN)

( * ) Notice: Subject to any disclaimer, the term of this patent is extended or adjusted under 35 U.S.C. 154(b) by 0 days.

(21) Appl. No.: 16/966,271

(22) PCT Filed: Jan. 18, 2019

(86) PCT No.: PCT/CN2019/072314
§ 371 (c)(1),
(2) Date: Jul. 30, 2020

(87) PCT Pub. No.: WO2019/149090
PCT Pub. Date: Aug. 8, 2019

(65) Prior Publication Data
US 2020/0369628 A1    Nov. 26, 2020

(30) Foreign Application Priority Data
Feb. 2, 2018    (CN) .......................... 201810106894.0

(51) Int. Cl.
*C07D 249/12*    (2006.01)
*A61K 9/00*    (2006.01)

(52) U.S. Cl.
CPC .......... *C07D 249/12* (2013.01); *A61K 9/0019* (2013.01); *A61K 9/0053* (2013.01); *C07B 2200/13* (2013.01)

(58) Field of Classification Search
CPC .................................................. C07D 249/12
See application file for complete search history.

(56) References Cited

U.S. PATENT DOCUMENTS

| 2018/0134670 A1 | 5/2018 | Zhao et al. |
| 2019/0233381 A1 | 8/2019 | Zhao et al. |

FOREIGN PATENT DOCUMENTS

| CN | 107540619 A | 1/2018 |
| CN | 108658879 A | 10/2018 |
| WO | 2016173503 A1 | 11/2016 |

OTHER PUBLICATIONS

International Search Report dated Apr. 24, 2019, issued in corresponding Application No. PCT/CN2019/072314, filed Jan. 18, 2019, 2 pages.
Lv, Yang, et al., Crystalline Drug, Polymorphic Drugs, Beijing: People's Medical Publishing House Co., LTD, First edition Oct. 2009, pp. 5-13.
Su, Desen, et al., Drug Polymorphs, Physicalpharmacy, Beijing: Chemical Industry Press Co., Ltd, First edition May 2004, pp. 17-18.
Xu, Longhua, et al., Crystal Anistrophy of Pegmatite Aluminosilicate Mineral and Its Flotation Application, Weijingyanxing Lüguisuanyan Kuangwujingti Gexiang Yixing Jiqi Fuxuan Yingyong, Beijing: Metallurgical Industry Press Co., Ltd, First edition, Jul. 2017, p. 27.

*Primary Examiner* — Shawquia Jackson
(74) *Attorney, Agent, or Firm* — Christensen O'Connor Johnson Kindness PLLC (57) ABSTRACT

The present invention provides a crystal form of urate transporter 1 inhibitor and a preparation method and use thereof. The crystal form is characterized by a stable state of appearance and a capability of further improving the purity and storage stability of the compound, etc., and suitable as a pharmaceutical raw material.

20 Claims, 4 Drawing Sheets

Figure 1

| No. | 2-theta (deg) | d (Å) | FWHM (deg) | Int. I (cps deg) | Phase name | Rel. int. I (a.u.) |
|---|---|---|---|---|---|---|
| 1 | 6.947(2) | 12.466(4) | 0.112(3) | 4131(45) | Unknown | 17.56 |
| 2 | 11.369(2) | 7.772(14) | 0.122(3) | 5997(44) | Unknown | 25.55 |
| 3 | 12.158(6) | 7.274(3) | 0.155(7) | 1471(38) | Unknown | 6.26 |
| 4 | 13.158(2) | 6.7182(11) | 0.106(3) | 5471(43) | Unknown | 23.28 |
| 5 | 13.445(7) | 6.580(4) | 0.097(17) | 243(24) | Unknown | 1.04 |
| 6 | 14.124(6) | 6.265(3) | 0.132(9) | 1261(29) | Unknown | 5.37 |
| 7 | 15.379(6) | 5.757(2) | 0.136(5) | 1134(33) | Unknown | 4.83 |
| 8 | 15.863(3) | 5.4634(10) | 0.176(2) | 3496(40) | Unknown | 14.88 |
| 9 | 16.433(4) | 5.4031(12) | 0.133(4) | 2217(37) | Unknown | 9.44 |
| 10 | 16.925(4) | 5.2343(11) | 0.142(11) | 834(76) | Unknown | 3.55 |
| 11 | 17.112(6) | 5.1776(19) | 0.124(7) | 1629(63) | Unknown | 6.93 |
| 12 | 17.707(4) | 5.0348(12) | 0.128(3) | 2414(40) | Unknown | 10.28 |
| 13 | 18.432(7) | 4.8092(7) | 0.134(2) | 9764(85) | Unknown | 41.65 |
| 14 | 18.918(4) | 4.6873(11) | 0.131(4) | 3962(68) | Unknown | 16.87 |
| 15 | 19.846(3)(17) | 4.470(34) | 0.156(14) | 24492(137) | Unknown | 100.00 |
| 16 | 20.207(2) | 4.3910(3) | 0.129(3) | 9028(528) | Unknown | 38.43 |
| 17 | 20.327(8)(17) | 4.3653(4) | 0.131(6) | 13115(588) | Unknown | 55.84 |
| 18 | 21.85(2) | 4.069(4) | 0.154(17) | 722(76) | Unknown | 3.07 |
| 19 | 22.141(3) | 3.9761(6) | 0.119(3) | 9679(126) | Unknown | 41.18 |
| 20 | 22.736(6) | 3.8910(10) | 0.173(6) | 9344(139) | Unknown | 39.77 |
| 21 | 23.696(4) | 3.7224(8) | 0.153(6) | 3065(152) | Unknown | 13.05 |
| 22 | 24.27(4) | 3.6634(7) | 0.163(11) | 8083(1030) | Unknown | 34.28 |
| 23 | 24.447(19) | 3.843(3) | 0.32(3) | 6206(1130) | Unknown | 26.41 |

CRYSTAL FORM OF URATE TRANSPORTER 1 INHIBITOR AND PREPARATION METHOD AND USE THEREOF

TECHNICAL FIELD

The invention relates to a crystal form of a urate transporter 1 (URAT1) inhibitor that can be used for the treatment of gout and hyperuricemia, and also relates to a preparation method for the crystal form and a pharmaceutical composition comprising the crystal form and use thereof.

BACKGROUND ART

The present inventors disclosed in WO2016173503 the following compound as a urate transporter 1 (URAT1) inhibitor: 2-((5-bromo-4-(4-bromonaphthalen-1-yl)methyl)-4H-1,2,4-triazol-3-yl)thio)acetic acid. For convenience, this compound is abbreviated as TY706 in the present application, and its structural formula is shown in Formula I. The compound can be used for preparing a medicament for treating gout and hyperuricemia. The present inventors disclosed a method for preparing the compound TY706 in CN201610506171.0.

Formula I

TY706

In further studies, the present inventors found that when the compound TY706 was separated from a solution by evaporation of the solvent at a later stage of the last preparation step, its physical form and appearance fluctuated from batch to batch, making it difficult to maintain a constant state of appearance and thus not suitable for direct use as a pharmaceutical raw material; and at the same time, the purity of the solid directly obtained by evaporation of the solvent fluctuated greatly, which results in a certain difficulty to the preparation of a pharmaceutical raw material with high purity.

CONTENTS OF THE INVENTION

Therefore, an object of the present invention is to provide a crystal form of the compound TY706, which is characterized by a stable state of appearance, high purity, storage stability, etc., and can be stably supplied as a pharmaceutical raw material. The crystal form described in the present invention may be simplified as the crystal form A of the compound TY706 in the present invention.

TY706

The crystalline form A of the compound TY706 of the present invention is characterized in that its powder X-ray diffraction (PXRD) pattern expressed by 2θ degree using Cu-Kα radiation has diffraction peaks at 18.432±1, 19.846±1, 20.207±1, 20.327±1, 22.341±1, 22.735±1, 25.654±1, 26.119±1, 26.617±1 and 33.159±1.

Preferably, the crystal form A of the compound TY706 of the present invention is characterized in that its powder X-ray diffraction pattern expressed by 2θ degree using Cu-Kα radiation has diffraction peaks at 18.432±1, 19.846±1, 20.207±1, 20.327±1, 22.341±1, 22.735±1, 24.276±1, 24.417±1, 25.654±1, 26.119±1, 26.617±1, 26.819±1, 27.427±1, 29.185±1, 30.223±1 and 33.159±1.

More preferably, the crystal form A of the compound TY706 of the present invention is characterized in that its powder X-ray diffraction pattern expressed by 2θ degree using Cu-Kα radiation has diffraction peaks at 6.547±1, 11.369±1, 12.158±1, 13.168±1, 14.124±1, 15.379±1, 15.868±1, 16.402±1, 16.925±1, 17.112±1, 17.707±1, 18.432±1, 18.918±1, 19.846±1, 20.207±1, 20.327±1, 21.88±1, 22.341±1, 22.735±1, 23.886±1, 24.276±1, 24.417±1, 24.994±1, 25.654±1, 26.119±1, 26.617±1, 26.819±1, 27.427±1, 27.692±1, 28.589±1, 28.982±1, 29.185±1, 29.640±1, 30.223±1 and 33.159±1.

Figure 1:
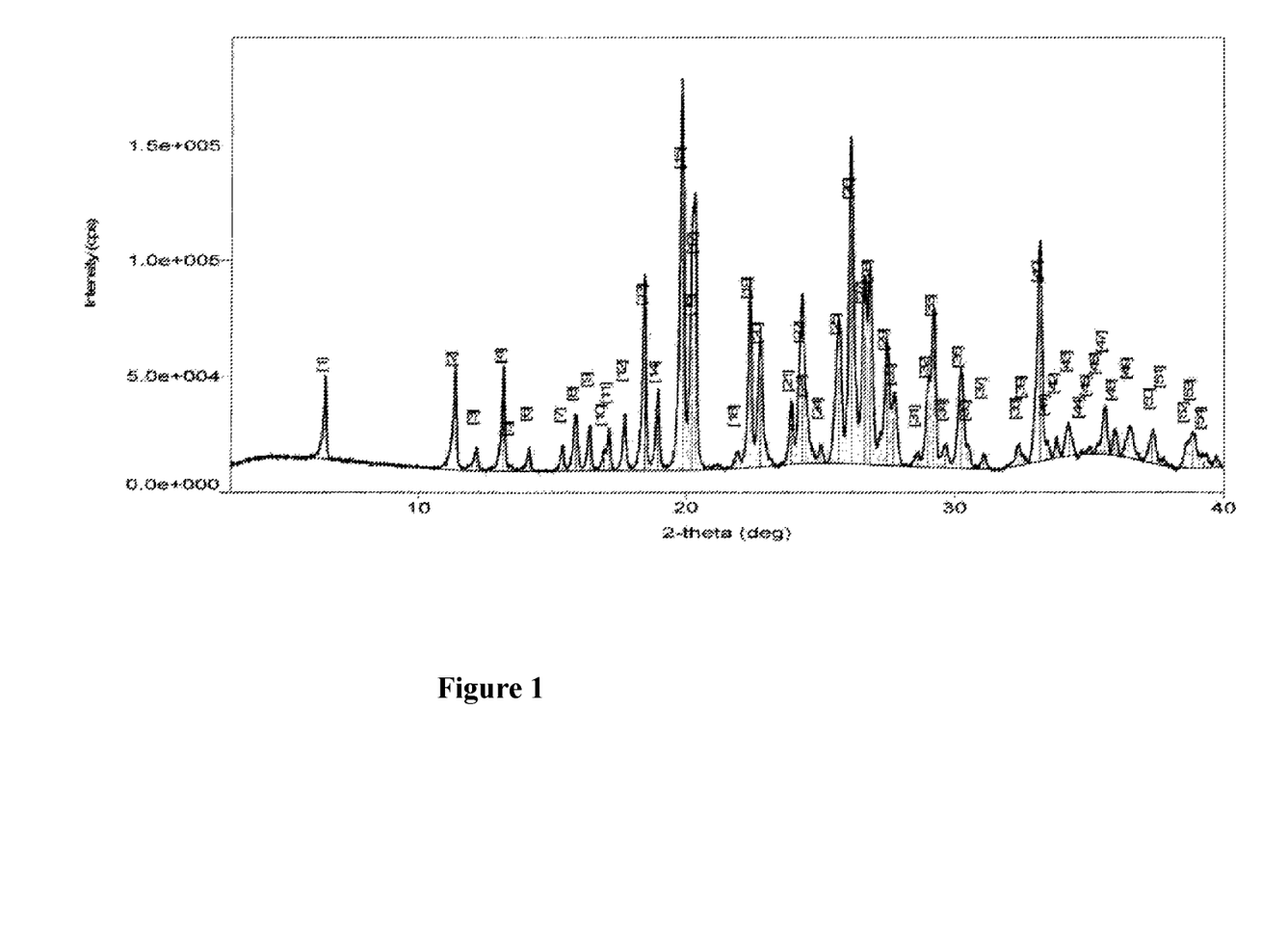
FIG. 1 is a powder X-ray diffraction (PXRD) pattern of the crystal form A of the compound TY706 of the present invention.

Most preferably, the crystal form A of the compound TY706 of the present invention is characterized in that its powder X-ray diffraction pattern expressed by 2θ degree using Cu-Kα radiation is shown in FIG. 1.

Specifically, the powder X-ray diffraction pattern of the crystal form A of the compound TY706 of the present invention expressed by 2θ degree using Cu-Kα radiation has d-spacings (Å) as shown in Table 1.

TABLE 1

D-spacings of powder X-ray diffraction characteristic peaks of the crystal form A of the compound TY706 of the present invention

| 2θ (°) | d-spacing (Å) | 2θ (°) | d-spacing (Å) | 2θ (°) | d-spacing (Å) |
|---|---|---|---|---|---|
| 6.547 | 13.489 | 18.918 | 4.687 | 26.119 | 3.409 |
| 11.369 | 7.777 | 19.846 | 4.470 | 26.617 | 3.346 |
| 12.158 | 7.274 | 20.207 | 4.391 | 26.819 | 3.322 |
| 13.168 | 6.718 | 20.327 | 4.365 | 27.427 | 3.249 |
| 14.124 | 6.265 | 21.88 | 4.059 | 27.692 | 3.219 |
| 15.379 | 5.757 | 22.341 | 3.976 | 28.589 | 3.120 |
| 15.868 | 5.580 | 22.735 | 3.908 | 28.982 | 3.078 |
| 16.402 | 5.400 | 23.886 | 3.722 | 29.185 | 3.057 |
| 16.925 | 5.234 | 24.276 | 3.663 | 29.640 | 3.012 |
| 17.112 | 5.178 | 24.417 | 3.643 | 30.223 | 2.955 |
| 17.707 | 5.005 | 24.994 | 3.560 | 33.159 | 2.700 |
| 18.432 | 4.810 | 25.654 | 3.470 | — | — |

The differential scanning calorimetry (DSC) analysis curve of the crystal form A of the compound TY706 of the present invention has an endothermic peak at 189.30° C.

The preparation method of the crystal form A of the compound TY706 of the present invention may include the steps of: mixing the compound TY706 with a single solvent or a mixed solvent, heating the mixture to reflux for 1-3 hours, then cooling it to room temperature, collecting the crystals by suction filtration, and drying them to obtain the crystal form A.

The single solvent may be selected from a $C_1$-$C_4$ lower alcohol such as methanol or ethanol; a $C_3$-$C_6$ lower ketone such as acetone or butanone; a $C_1$-$C_3$ lower acid such as acetic acid; tetrahydrofuran; 1,4-dioxane; a lower ester synthesized from a $C_1$-$C_4$ lower acid and a $C_1$-$C_4$ lower alcohol such as ethyl acetate, methyl acetate, butyl acetate, ethyl formate, butyl formate or ethyl butyrate; diethyl ether, methyl tert-butyl ether, diisopropyl ether; a $C_5$-$C_8$ linear or branched alkane such as n-hexane; or a $C_5$-$C_8$ cycloalkane.

The mixed solvent may be a mixture composed of two or more of the above-described single solvents, for example, a mixture of ethyl acetate and n-hexane in a volume ratio of 1:1, a mixture of acetone and n-hexane in a volume ratio of 1:1, or a mixture of tetrahydrofuran and n-hexane in a volume ratio of 1:1.

The physical form and appearance of the sample obtained by separating the compound TY706 from a solution by evaporation of the solvent fluctuates from batch to batch, making it difficult to maintain a constant state of appearance; due to a large variation range, it is not suitable for direct use as a pharmaceutical raw material. However, the crystal form A of TY706 disclosed in the present disclosure is characterized by a stable state of appearance, high purity, stable storage, etc., and can be stably supplied to the preparation of a pharmaceutical raw material, and thus has an industrial practicality.

The crystalline form A of the compound TY706 described in the present invention is stable over more than 10 batches prepared continuously in a synthesis scale ranging from 1 g to 500 g, and has an appearance of white crystalline solid. As confirmed by powder X-ray diffraction (PXRD) and Differential Scanning Calorimetry (DSC) analysis, its crystal form in each batch is the crystal form A. HPLC analysis for each batch shows that the purity of the crystal form A is significantly higher than that of the raw material used to prepare the crystal form A. In a two-week influencing factor test, the crystal form A shows a certain stability to light, heat and moisture.

The invention also provides a pharmaceutical composition comprising the crystal form A of the compound TY706 and optionally a pharmaceutically acceptable adjuvant. The crystal form A of the compound TY706 of the present invention can be formulated together with one or more pharmaceutically acceptable carriers, excipients or diluents into a pharmaceutical composition. The pharmaceutical composition may be in the dosage form of an oral solid preparation, an oral liquid preparation or an injection, etc. The oral solid preparation may be a dispersible tablet, an enteric-coated tablet, a chewable tablet, an orally disintegrating tablet, a capsule or a granule; the oral liquid preparation is an oral solution; and the injection is a liquid injection, a lyophilized powder for injection, a large-volume infusion solution or a small-volume infusion solution, etc.

The pharmaceutical composition of the present invention may comprise one or more pharmaceutically acceptable adjuvants selected from a filler, a binder, a disintegrant, a lubricant, a glidant, an effervescent agent, a flavoring agent, a preservative, a coating material or an excipient.

Specifically, the filler is selected from one or more of lactose, sucrose, dextrin, starch, pregelatinized starch, mannitol, sorbitol, calcium hydrogen phosphate, calcium sulfate, calcium carbonate or microcrystalline cellulose; the binder is selected from one or more of sucrose, starch, povidone, sodium carboxymethyl cellulose, hypromellose, hydroxypropyl cellulose, methyl cellulose, polyethylene glycol, pharmaceutically acceptable ethanol or water; and the disintegrant is selected from one or more of starch, crospovidone, croscarmellose sodium, low-substituted hydroxypropyl cellulose, sodium carboxymethyl cellulose or effervescent disintegrant.

The crystal form A of the compound TY706 of the present invention has an inhibitory effect on human urate transporter 1 (URAT1), and can be used as an effective ingredient in the preparation of a therapeutic medicament for gout and hyperuricemia. The activity of the crystal form A of TY706 of the present invention is verified by an in vitro model for inhibition of humanized URAT1. Thus, the present invention provides use of the crystal form A of the compound TY706 or a pharmaceutical composition comprising the crystal form A of the compound TY706 in the preparation of a medicament for the treatment of gout and/or hyperuricemia.

The crystal form A of the compound TY706 of the present invention is effective over a relatively wide dosage range. For example, the daily administration dose is in a range of 1 mg-500 mg/individual and can be administered one time or several times. The actual dosage for the crystal form A of the compound TY706 of the present invention can be determined by a doctor according to the relevant conditions, including the physical state of the individual being treated, the route of administration, age, weight, individual response to the drug, the severity of symptoms, etc.

BRIEF DESCRIPTION OF THE DRAWINGS

FIG. 2 shows powder X-ray diffraction data of the crystal form A of the compound TY706 of the present invention.

BEST MODES FOR CARRYING OUT THE INVENTION

The present invention will be further described below with reference to the examples. It should be noted that the following examples are only for illustration, and not meant to limit the present invention. Various changes made by those skilled in the art in light of the teaching of the present invention shall fall within the protection scope claimed by the claims of the present application.

The conditions for differential scanning calorimetry (DSC) analysis for the determination of the crystal form A of the compound TY706 used in the present invention were as follows: the weight of sample of the crystal form A of the compound TY706 was 8.8900 mg, the heating rate was 10° C./min, the scanning temperature range was 30.0-220.0° C., the reference substance was $Al_2O_3$, and the instrument used was Mettler Toledo DSC822e TG/DSC analyzer.

The powder X-ray diffraction (PXRD) analysis data for the determination of the crystal form A of the compound TY706 used in the present invention were measured on SmartLab 3KW powder diffractometer, Rigaku Corporation, Japan. The tube voltage for generating X-rays was 40 KV, the tube current was 40 mA, the target was Cu-Kα, 2θ=3.0000-40.0000°, and the scanning speed was 10.4018°/min.

The HPLC conditions for the determination of the crystal form A of the compound TY706 and its raw material in the present invention were as follows: chromatographic column: C18, 5 μu, Φ4.6×150 mm, Waters Atlantis T3; mobile phase A: acetonitrile-methanol=9:1, mobile phase B: 10 mM diammonium hydrogen phosphate (pH was adjusted to 4.30±0.03 with phosphoric acid), gradient elution (Table 2); detection wavelength: 225 nm; column temperature: 35° C.; flow rate: 1.0 mL/min; sample concentration: 0.3 mg/mL; injection volume: 15 μL; solvent for dissolving: phosphate buffer (pH 7.8-8.0; prepared by dissolving 5.59 g of dipotassium hydrogen phosphate and 0.41 g of potassium dihydrogen phosphate by adding water to a volume of 1000 mL).

TABLE 2

Gradient elution of HPLC test for TY706

| Mobile phase | A | B |
|---|---|---|
| 0 | 25 | 75 |
| 30 | 40 | 60 |
| 45 | 50 | 50 |
| 60 | 70 | 30 |
| 70 | 70 | 30 |
| 71 | 25 | 75 |
| 75 | 25 | 75 |

Example 1

Preparation of the Crystal Form A of TY706

(1) The compound TY706 of the present invention can be prepared by the following steps:

TY706 can be prepared according to the preparation method disclosed in CN 201610506171.0, and the specific scheme is as follows:

TY706

Step 1: Synthesis of Compound 2

To a 1 L dry round bottom flask were added Compound 1 (1-methylnaphthalene, 28.44 g, 200 mmol), NBS (42.72 g, 240 mmol) and MeCN (700 mL), and the resulting mixture was stirred at 30° C.-40° C. for 12 hours.

The reaction mixture was cooled to room temperature, poured into ice water (3 L), and extracted with dichloromethane (500 mL×3). The extract phases were combined and washed successively with 5% $Na_2CO_3$ aqueous solution (500 mL×5), 10% $Na_2S_2O_3$ aqueous solution (500 mL) and 5% saline solution (500 mL), and dried over anhydrous $Na_2SO_4$. The solvent of the dried organic phase was distilled off on a rotary evaporator, and the obtained residue was subjected to column chromatography for purification to obtain Product 2 as a colorless oil, 39.80 g, yield: 90%.

$^1$H NMR (DMSO-$d_6$, 400 MHz), δ 8.14-8.16 (m, 1H), 8.07-8.09 (m, 1H), 7.76 (d, 1H, J=7.6 Hz), 7.66-7.70 (m, 2H), 7.30 (d, 1H, J=7.6 Hz), 2.63 (s, 3H).

Step 2: Synthesis of Compound 3

To a dry 1 L round bottom flask was added n-hexane (400 mL) at room temperature, and Compound 2 (35.37 g, 160 mmol), benzoyl peroxide (BPO, 0.775 g, 3.2 mmol) and NBS (34.17 g, 192 mmol) were added with stirring. The mixture was stirred and heated to reflux until the reaction was completed as shown by TLC (0.775 g of BPO was added every 8 hours after the reaction started; and the reaction was usually completed within 36 hours).

After completion of the reaction, the system was cooled to room temperature, stirred for 2 hours, and then suction filtered. The filter cake was added to 800 mL of water, stirred at room temperature for 1 hour, and suction filtered, and the filtrate was discarded. The filter cake was added to 800 mL of water again and stirred for 1 hour at room temperature, and was suction filtered, and the filtrate was discarded. The obtained filter cake was slurried by stirring with 800 mL of n-hexane for 2 hours, and suction filtered, and the filter cake was dried to obtain pure Compound 3 as a white solid, 34.56 g, yield: 72%. Melting point: 104.0-105.5° C.

$^1$H NMR (DMSO-$d_6$, 400 MHz), δ 8.20-8.26 (m, 2H), 7.86 (d, 1H, J=8.0 Hz), 7.72-7.78 (m, 2H), 7.62 (d, 1H, J=7.6 Hz), 5.21 (s, 2H).

Step 3: Synthesis of Compound 4

Compound 3 (30.00 g, 100 mmol) was added to a dry 1 L round bottom flask, dissolved in dry DMF (300 mL), and then heated to 140° C. under stirring, and KSCN (11.66 g, 120 mmol) was added in three batches within 1 minute. After completion of the addition, the reaction mixture was continued to be stirred at 140° C. for 1 hour.

After being cooled to room temperature, the reaction mixture was poured into stirring ice water (2000 mL), stirred, and extracted with $CH_2Cl_2$ (300 mL×3). The organic phases were combined, washed with 5% saline solution (200 mL×5), and dried over anhydrous $Na_2SO_4$. The solvent of the dried organic phase was distilled off on a rotary evaporator, and the obtained residue was subjected to column chromatography for purification to obtain Compound 4 as a white solid, 25.59 g, yield: 92%. Melting point: 94.5-97.5° C.

$^1$H NMR (DMSO-$d_6$, 400 MHz), δ 8.21-8.24 (m, 1H), 8.11-8.14 (m, 1H), 7.92 (d, 1H, J=7.6 Hz), 7.73-7.78 (m, 2H), 7.52 (d, 1H, J=8.0 Hz), 5.41 (s, 2H).

Step 4: Synthesis of Compound 5 and Compound 6

The above crude Compound 4 (6.95 g, calculated as 25 mmol) was dissolved in THF (100 mL), and stirred at room temperature. Formyl hydrazide (1.80 g, 30 mmol) was added, and then stirring was continued overnight, at which point the reaction was completed as tested by TLC.

The reaction mixture was evaporated to dryness on a rotary evaporator. The resulting residue was crude Compound 5, which was dissolved in DMF (80 mL), and a solution prepared from solid $K_2CO_3$ (3.46 g, 25 mol) and water (10 mL) was added. The reaction mixture was stirred at 50° C. until the reaction was completed (usually 5 hours).

After being cooled to room temperature, the reaction mixture was poured into ice water (400 mL), stirred, adjusted to pH=5-6 with hydrochloric acid, and extracted with $CH_2Cl_2$ (150 mL×5). The organic phases were combined, washed with 5% saline solution (200 mL), and dried over anhydrous $Na_2SO_4$. The solvent of the dried organic phase was distilled off on a rotary evaporator, and the resulting residue was subjected to column chromatography for purification to obtain Product F as a white solid. $^1$H NMR showed that it contained about 5% of debrominated by-product therein. The crude Product F was crystallized twice from ethyl acetate to obtain pure Compound 6, 6.96 g, yield: 87% (a total yield from Compound 4 to Compound 6). Melting point: 243-244° C.

$^1$H NMR (DMSO-$d_6$, 400 MHz), δ 13.88 (brs, 1H), 8.37 (s, 1H), 8.22 (d, 2H, J=7.6 Hz), 7.90 (d, 1H, J=7.2 Hz), 7.72 (m, 2H), 7.18 (d, 1H, J=7.2 Hz), 5.61 (s, 2H).

Step 5: Synthesis of Compound 7

Compound 6 (6.40 g, 20 mmol) was dissolved in DMF (100 mL) and stirred at room temperature. Solid $K_2CO_3$ (8.29 g, 60 mmol) and methyl bromoacetate (3.67 g, 24 mmol) were added. The resulting reaction mixture was continued to be stirred at room temperature until the reaction was completed as tested by TLC (usually within 5 hours).

The reaction mixture was poured into ice water (400 mL), stirred, and extracted with $CH_2Cl_2$ (100 mL×5). The organic phases were combined, washed with 5% saline solution (200 mL), and dried over anhydrous $Na_2SO_4$. The solvent of the dried organic phase was distilled off on a rotary evaporator, and the obtained residue was subjected to column chromatography for purification to obtain Compound 7 as a white solid, 7.37 g, yield: 94%. Melting point: 112.5-114° C.

$^1$H NMR (DMSO-$d_6$, 400 MHz), δ 8.67 (s, 1H), 8.22-8.25 (m, 1H), 8.15-8.17 (m, 1H), 7.88 (d, 1H, J=7.6 Hz), 7.72-7.79 (m, 2H), 6.92 (d, 1H, J=7.6 Hz), 5.72 (s, 2H), 4.07 (s, 2H), 3.62 (s, 3H).

Step 6: Synthesis of Compound 8

Compound 7 (3.92 g, 10 mmol) was dissolved in acetonitrile (50 mL), and stirred at room temperature. NBS (2.14 g, 12 mmol) was added, and stirring was continued at room temperature until the reaction was completed as tested by TLC (usually within 12 hours).

The reaction mixture was poured into ice water (200 mL), stirred, and extracted with $CH_2Cl_2$ (100 mL×3). The organic phases were combined, washed sequentially with a saturated Na₂CO₃ solution (100 mL×3) and 5% saline solution (200 mL), and dried over anhydrous Na₂SO₄. The solvent of the dried organic phase was distilled off on a rotary evaporator, and the obtained residue was subjected to column chromatography for purification to obtain Product 8 as a white solid, melting point: 141-143° C., 3.49 g, yield: 74%.

$^1$H NMR (DMSO-$d_6$, 400 MHz), δ 8.21-8.26 (m, 2H), 7.84 (d, 1H, J=8.0 Hz), 7.76-7.82 (m, 2H), 6.49 (d, 1H, J=7.6 Hz), 5.74 (s, 2H), 4.08 (s, 2H), 3.61 (s, 3H).

Step 7: Synthesis of TY706

Compound 8 (3.30 g, 7 mmol) was added to methanol (50 mL), and stirred at room temperature. A solution prepared from LiOH.H₂O (0.84 g, 20 mmol) and water (3 mL) was added, and then the mixture was stirred at room temperature until the reaction was completed as detected by TLC (usually 2 hours).

The reaction mixture was poured into ice water (200 mL), stirred, adjusted to pH=2-3 with hydrochloric acid, and extracted with CH₂Cl₂ (100 mL×4). The organic phases were combined, washed with 5% saline solution (200 mL), and dried over anhydrous Na₂SO₄. The solvent of the dried organic phase was distilled off on a rotary evaporator, and the obtained residue was subjected to column chromatography for purification to obtain the product TY706, which was a white solid, 2.82 g, yield: 88%. Melting point: 169.5-171.5° C.

$^1$H NMR (DMSO-$d_6$, 400 MHz), δ 12.97 (brs, 1H), 8.22-8.26 (m, 2H), 7.83 (d, 1H, J=8.0 Hz), 7.76-7.81 (m, 2H), 6.51 (d, 1H, J=8.0 Hz), 5.73 (s, 2H), 4.01 (s, 2H).

Figure 3:
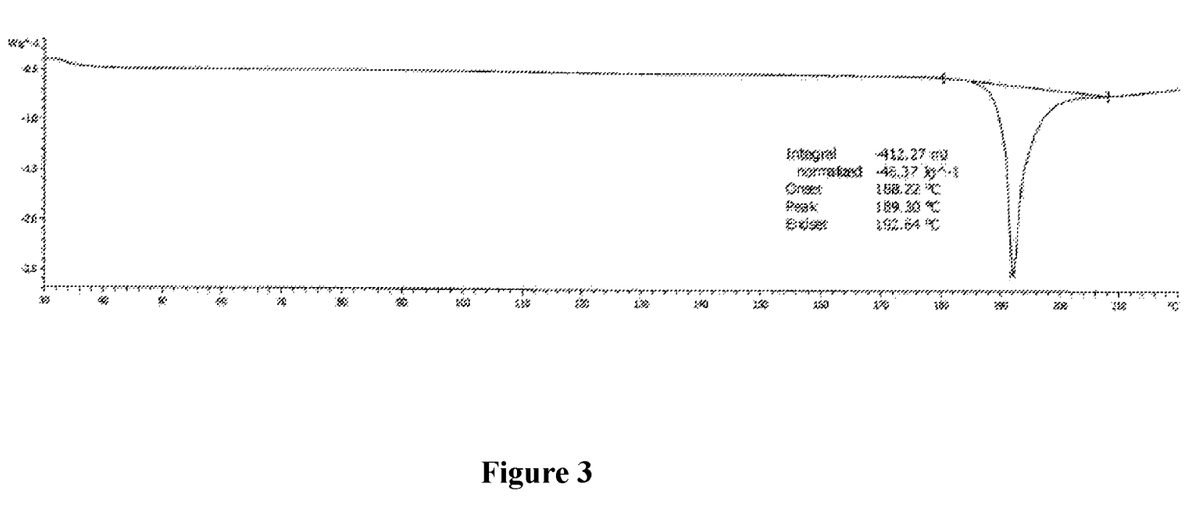
FIG. 3 shows a differential scanning calorimetry (DSC) analysis curve of the crystal form A of the compound TY706 of the present invention.

(2) The crystal form A of the compound TY706 of the present invention can be prepared by the following method:

20.00 g of the compound TY706 was placed in a 500 mL round bottom flask, to which was added 200 mL of acetone, and the mixture was stirred under reflux for 3 hours. Then, it was naturally cooled to room temperature under stirring. The solid was collected by suction filtration and dried on a vacuum oil pump at 25° C. for 12 hours to obtain the crystal form A of the compound TY706 of the present invention, 19.00 g, recovery rate: 95%. It was confirmed to be the crystal form A by powder X-ray diffraction (PXRD) and differential scanning calorimetry (DSC) analysis. FIGS. 1 and 2 are powder X-ray diffraction (PXRD) pattern and data of the crystal form A of the compound TY706 of the present invention, respectively. FIG. 3 is a differential scanning calorimetry (DSC) pattern of the crystal form A of the compound TY706 of the present invention.

Examples 2-18

Preparation of the Crystal Form A of TY706

According to the method for preparing the crystal form A of the compound TY706 in Example 1, the following results were obtained by exchanging for other solvents or solvent mixtures (Table 3).

TABLE 3

Examples 2-18: Results of preparation of the crystal form A of the compound TY706 by exchanging for different solvents

| Examples | Initial adding amount of TY706 | Solvent | Recovery rate | Crystal form |
|---|---|---|---|---|
| 2 | 20.00 g | butanone | 96% | A |
| 3 | 20.00 g | methanol | 90% | A |
| 4 | 20.00 g | ethanol | 92% | A |
| 5 | 20.00 g | ethyl acetate | 94% | A |
| 6 | 20.00 g | methyl acetate | 93% | A |
| 7 | 20.00 g | butyl acetate | 95% | A |
| 8 | 20.00 g | ethyl formate | 94% | A |
| 9 | 20.00 g | butyl formate | 96% | A |
| 10 | 20.00 g | ethyl butyrate | 96% | A |
| 11 | 20.00 g | diisopropyl ether | 97% | A |
| 12 | 20.00 g | acetic acid | 90% | A |
| 13 | 20.00 g | tetrahydrofuran | 88% | A |
| 14 | 20.00 g | 1,4-dioxane | 85% | A |
| 15 | 20.00 g | n-hexane | 98% | A |
| 16 | 20.00 g | ethyl acetate/n-hexane (a volume ratio of 1:1) | 97% | A |
| 17 | 20.00 g | acetone/n-hexane (a volume ratio of 1:1) | 96% | A |
| 18 | 20.00 g | tetrahydrofuran/n-hexane (a volume ratio of 1:1) | 96% | A |

Example 19

| Ingredient | Dosage/tablet |
|---|---|
| Sample of Example 1 | 5 mg |
| Microcrystalline cellulose | 80 mg |
| Pregelatinized starch | 70 mg |
| Polyvinylpyrrolidone | 6 mg |
| Sodium carboxymethyl starch | 5 mg |
| Magnesium stearate | 2 mg |
| Talc | 2 mg |

The active ingredient, pregelatinized starch and microcrystalline cellulose were sieved and mixed thoroughly, and a polyvinylpyrrolidone solution was added and mixed. The soft material was prepared, sieved, prepared into wet granules, and dried at 50-60° C. Sodium carboxymethyl starch, magnesium stearate and talc were sieved in advance, and then added to the above granules for tabletting.

Example 20

The $IC_{50}$ value of URAT1 inhibition for the crystalline form A of TY706 of the present invention was determined according to the following method:

After trypsin digestion, both the expression cells (HEK293) that stably express the URAT1 gene and mock cells were seeded into a lysine-coated 24-well culture plate with a cell seeding density of $1 \times 10^5$ cells/well, and cultured in an incubator with 5% $CO_2$ at 37° C. under saturated humidity for 2 days. The culture medium was removed from the culture plate, and the cultured cells were washed twice with DPBS, and incubated in DPBS buffer at 37° C. for 10 min 500 μL of solutions containing radio-labeled probe substrate ([8-$^{14}$C] uric acid) and a series of concentrations (0.001-10 μM) of the test compounds or a blank solution were then used to replace DPBS. The concentration of [8-$^{14}$C] uric acid was 30 μM, and the radiation intensity was 0.867 μCi per well. After 2 min, the reaction was terminated with DPBS buffer solution in ice bath and washed 3 times. Then, 500 μL of 0.1 mol/L NaOH was added to each well to lyse the cells, and the lysate was extracted into a scintillation vial. 3 mL of scintillation liquid (Aquasol-2) was added, and Tri-Carb 2910TR liquid scintillation counter (PerkinElmer, Waltham, USA) was used to determine the radiation intensity in the sample.

The inhibition rates of URAT1 for the test compounds were calculated according to the following formula by using the data measured above:

Inhibition rate=(control-test compound)/(control-mock)×100% wherein control=the radiation intensity corresponding to the well without the test compound test compound=the radiation intensity corresponding to the well with the test compound mock=the radiation intensity corresponding to the well with blank cells that were not transfected with URAT1

The determination results are shown in Table 4.

TABLE 4

Experimental results of in vitro inhibition of URAT1 for TY706 and lesinurad

| Compound | IC$_{50}$ (hURAT1, μM) |
|---|---|
| TY706 | 0.081 |
| lesinurad | 7.18 |

The above IC$_{50}$ determination results show that the crystal form A of the compound TY706 has a strong inhibitory effect on human URAT1, with an in vitro activity higher than that of lesinurad, a urate transporter 1 (URAT1) inhibitor by about two orders of magnitude, and can be used to prepare a medicament for the treatment of gout and hyperuricemia.

Example 21

Purity Measurement for the Sample of the Crystal Form A of TY706

In Example 1, the HPLC purity of the sample of the crystal form A of TY706 of the present invention is 99.76%, with 4 impurities being contained therein, while the HPLC purity of the TY706 raw material used for preparing the crystal form A is 99.31%, with 11 impurities being contained therein. It can be seen from this that the purity of the crystal form A is significantly improved, and thus suitable for the production of TY706 pharmaceutical raw material.

Example 22

Influencing Factor Tests for the Sample of the Crystal Form A of TY706

The sample of the crystal form A of TY706 prepared in Example 1 and the raw material for the preparation of the crystal form A were simultaneously subjected to influencing factor tests, and they were respectively placed under the conditions of illumination (5000 Lx·hr, with the weighing bottle being placed open), high heat (60° C., with the weighing bottle being placed open), and high humidity (92.5% RH, with the weighing bottle being placed open) for 14 days, and the appearance and the number and total amount of impurities (determined by HPLC) were compared with those measured on day 0, and the results are shown in Table 5-7.

TABLE 5

Test data for stability of the crystal form A of TY706 to light

| Time (days) | Samples | Appearance | Number of impurities | Total amount of impurities | Crystal form |
|---|---|---|---|---|---|
| 0 | TY706 raw material | White solid | 11 | 0.69% | — |
|  | Crystal form A of TY706 | White solid | 4 | 0.24% | A |
| 7 | TY706 raw material | White solid | 13 | 1.13% | — |
|  | Crystal form A of TY706 | White solid | 6 | 0.28% | A |
| 14 | TY706 raw material | Light yellow solid | 25 | 2.68% | — |
|  | Crystal form A of TY706 | White solid | 7 | 0.41% | A |

TABLE 6

Test data of stability of the crystal form A of TY706 to high heat

| Time (days) | Samples | Appearance | Number of impurities | Total amount of impurities | Crystal form |
|---|---|---|---|---|---|
| 0 | TY706 raw material | White solid | 11 | 0.69% | — |
|  | Crystal form A of TY706 | White solid | 4 | 0.24% | A |
| 7 | TY706 raw material | White solid | 12 | 0.78% | — |
|  | Crystal form A of TY706 | White solid | 4 | 0.25% | A |
| 14 | TY706 raw material | White solid | 15 | 1.19% | — |
|  | Crystal form A of TY706 | White solid | 5 | 0.26% | A |

TABLE 7

Test data of the stability of the crystal form A of TY706 to high humidity

| Time (days) | Samples | Appearance | Number of impurities | Total amount of impurities | Crystal form |
|---|---|---|---|---|---|
| 0 | TY706 raw material | White solid | 11 | 0.69% | — |
|  | Crystal form A of TY706 | White solid | 4 | 0.24% | A |
| 7 | TY706 raw material | White solid | 12 | 0.72% | — |
|  | Crystal form A of TY706 | White solid | 4 | 0.24% | A |
| 14 | TY706 raw material | White solid | 14 | 0.84% | — |
|  | Crystal form A of TY706 | White solid | 4 | 0.25% | A |

It can be seen from the above data that the stabilities of the crystal form A of TY706 to light, high heat or high humidity are all higher than those of the raw material for preparing the crystal form A of TY706, demonstrating that the crystal form A of TY706 is suitable for the production of TY706 pharmaceutical raw material.

Although the present invention has been described to a certain extent, it is obvious that various conditions can be appropriately changed without departing from the spirit and scope of the present invention. It is understood that the present invention is not limited to the described embodiments, but falls within the scope of the claims, which includes equivalent replacements for each of the elements described.

The invention claimed is:

1. A crystal form of a compound represented by Formula I, characterized in that its powder X-ray diffraction pattern expressed by 2θ degree using Cu-Kα radiation has diffraction peaks at 18.432±1, 19.846±1, 20.207±1, 20.327±1, 22.341±1, 22.735±1, 25.654±1, 26.119±1, 26.617±1 and 33.159±1,

I

2. The crystal form according to claim 1, characterized in that its powder X-ray diffraction pattern expressed by 2θ degree using Cu-Kα radiation has diffraction peaks at 18.432±1, 19.846±1, 20.207±1, 20.327±1. 22.341±1, 22.735±1, 24.276±1, 24.417±1, 25.654±1, 26.119±1, 26.617±1, 26.819±1, 27.427±1, 29.185±1, 30.223±1 and 33.159±1.

3. The crystal form according to claim 1, characterized in that its differential scanning calorimetry analysis curve has an endothermic peak at 189.30° C.

4. A method for preparing the crystal form according to claim 1, characterized in comprising mixing the compound represented by Formula I with a single solvent or a mixed solvent, heating the mixture to reflux for 1-3 hours, then cooling it to room temperature, collecting the crystals by suction filtration, and drying them to obtain the crystal form.

5. The method according to claim 4, characterized in that the single solvent is selected from a $C_1$-$C_4$ lower alcohol; a $C_3$-$C_6$ lower ketone; a $C_1$-$C_3$ lower acid; tetrahydrofuran; 1,4-dioxane; a lower ester synthesized from a $C_1$-$C_4$ lower acid and a $C_1$-$C_4$ lower alcohol; diethyl ether, methyl tert-butyl ether, diisopropyl ether; a $C_5$-$C_8$ linear and branched alkane; or a $C_5$-$C_8$ cycloalkane.

6. A pharmaceutical composition, characterized in that it comprises the crystal form according to claim 1 and optionally a pharmaceutically acceptable adjuvant.

7. The pharmaceutical composition according to claim 6, characterized in that it is an oral solid preparation, an oral liquid preparation or an injection.

8. The pharmaceutical composition according to claim 6, characterized in that the pharmaceutically acceptable adjuvant is selected from one or more of a filler, a binder, a disintegrant, a lubricant, a glidant, an effervescent agent, a flavoring agent, a preservative, a coating material or an excipient.

9. A method for treating gout, comprising administering a therapeutically effective amount of a crystal form of claim 1 to a subject in need thereof.

10. A method for treating hyperuricemia, comprising administering a therapeutically effective amount of a crystal form of claim 1 to a subject in need thereof.

11. The crystal form according to claim 1, characterized in that its powder X-ray diffraction pattern expressed by 2θ degree using Cu-Kα radiation has diffraction peaks at 6.547±1, 11.369±1, 12.158±1, 13.168±1, 14.124±1, 15.379±1, 15.868±1, 16.402±1, 16.925±1, 17.112±1, 17.707±1, 18.432±1, 18.918±1, 19.846±1, 20.207±1, 20.327±1, 21.88±1, 22.341±1, 22.735±1, 23.886±1, 24.276±1, 24.417±1, 24.994±1, 25.654±1, 26.119±1, 26.617±1, 26.819±1, 27.427±1, 27.692±1, 28.589±1, 28.982±1, 29.185±1, 29.640±1, 30.223±1, and 33.159±1.

12. The method according to claim 4, characterized in that the single solvent is selected from methanol, ethanol, acetone, butanone, acetic acid, tetrahydrofuran, 1,4-dioxane, methyl acetate, ethyl acetate, butyl acetate, ethyl formate, butyl formate, ethyl butyrate, diisopropyl ether or n-hexane.

13. The method according to claim 4, characterized in that the $C_1$-$C_4$ lower alcohol is methanol or ethanol.

14. The method according to claim 4, characterized in that the $C_3$-$C_6$ lower ketone is acetone or butanone.

15. The method according to claim 4, characterized in that the $C_1$-$C_3$ lower acid is acetic acid.

16. The method according to claim 4, characterized in that the lower ester synthesized from a $C_1$-$C_4$ lower acid and a $C_1$-$C_4$ lower alcohol is ethyl acetate, methyl acetate, butyl acetate, ethyl formate, butyl formate or ethyl butyrate.

17. The method according to claim 4, characterized in that the $C_5$-$C_8$ linear is n-hexane.

18. The method according to claim 4, characterized in that the mixed solvent is a mixture composed of two or more of said single solvents.

19. The method according to claim 4, characterized in that the mixed solvent is a mixture of ethyl acetate and n-hexane in a volume ratio of 1:1, a mixture of acetone and n-hexane in a volume ratio of 1:1, or a mixture of tetrahydrofuran and n-hexane in a volume ratio of 1:1.

20. The pharmaceutical composition according to claim 6, characterized in that it is a dispersible tablet, an enteric-coated tablet, a chewable tablet, an orally disintegrating tablet, a capsule or a granule; an oral solution; a liquid injection, a lyophilized powder for injection, a large-volume infusion solution, or a small-volume infusion solution.

* * * * *